United States Patent
Kim et al.

(10) Patent No.: US 7,871,572 B2
(45) Date of Patent: Jan. 18, 2011

(54) CHEMICAL SENSORS BASED ON METAL NANOPARTICLE ENCAPSULATED BY MIXED LIGAND AND SENSOR ARRAY

(75) Inventors: Young Jun Kim, Daejeon-Shi (KR); Yong Shin Kim, Daejeon-Shi (KR); Yoon Seok Yang, Seongnam-Shi (KR); Seung Chul Ha, Suwon-Shi (KR); Hae Sik Yang, Daejeon-Shi (KR); Yun Tae Kim, Daejeon-Shi (KR); Dae Sik Lee, Daejeon-Shi (KR); Young Sik Hong, Daejeon-Shi (KR)

(73) Assignee: Electronics and Telecommunications Research Instutute, Daejon-Shi (KR)

( * ) Notice: Subject to any disclaimer, the term of this patent is extended or adjusted under 35 U.S.C. 154(b) by 1082 days.

(21) Appl. No.: 10/944,939

(22) Filed: Sep. 21, 2004

(65) Prior Publication Data
US 2005/0142030 A1 Jun. 30, 2005

(30) Foreign Application Priority Data
Dec. 26, 2003 (KR) ...................... 10-2003-0097067

(51) Int. Cl.
G01N 27/04 (2006.01)
G01N 27/22 (2006.01)
G01N 33/00 (2006.01)
G01N 33/553 (2006.01)

(52) U.S. Cl. .................. 422/82.02; 422/82.01; 422/83; 422/88; 422/90; 422/98; 436/131; 436/132; 436/139; 436/140; 436/149; 436/151; 436/525

(58) Field of Classification Search ... 422/82.01–82.04, 422/83, 88, 90, 93, 98; 436/139–140, 149, 436/151, 183, 524–525, 131–132
See application file for complete search history.

(56) References Cited

U.S. PATENT DOCUMENTS 6,221,673 B1 4/2001 Snow et al.

(Continued)

FOREIGN PATENT DOCUMENTS

WO 00/00808 1/2000

OTHER PUBLICATIONS

Bain, C. D. et al, Journal of the American Chemical Society 1988, 110, 6560-6561.*

(Continued)

*Primary Examiner*—Arlen Soderquist
(74) *Attorney, Agent, or Firm*—Lowe Hauptman Ham & Berner LLP

(57) ABSTRACT

Provided are mixed ligand metal nanoparticle chemical sensors in which metal nanoparticles are encapsulated by at least two kinds of different molecule ligands having a relatively low conductivity and various composition ratios, and a chemical sensor array in which a film of the metal nanoparticle sensor is formed on the substrate. The metal nanoparticle sensor using the mixed ligand improves sensitivity and reaction speed with respect to an analyte, and selectivity with respect to various analytes, and a kind and a composition of a ligand of the mixed ligand constituting the metal nanoparticle sensor are adjusted to allow the high sensitivity nanoparticle sensor to be applied to the sensor array technology, thereby enabling a design of sensor properties as well as systematic access to a configuration of the sensor array the most efficient for the analytes.

2 Claims, 3 Drawing Sheets

U.S. PATENT DOCUMENTS

| | | | |
|---|---|---|---|
| 6,458,327 B1 | 10/2002 | Vossmeyer | |
| 6,537,498 B1 | 3/2003 | Lewis et al. | |
| 2004/0018633 A1* | 1/2004 | Foos et al. | 436/166 |
| 2004/0029288 A1* | 2/2004 | Snow et al. | 436/149 |
| 2004/0058457 A1* | 3/2004 | Huang et al. | 436/524 |

OTHER PUBLICATIONS

Chidsey, C. E. D., Science 1991, 251, 919-922.*
Laibinis, P. E. et al, Langmuir 1991, 7, 3167-3173.*
Chailapakul, O. et al, Langmuir 1993, 9, 884-888.*
Biebuyck, H. A. et al, Langmuir 1993, 9, 1766-1770.*
Terrill, R. H. et al, Journal of the American Chemical Society 1995, 117, 12537-12548.*
Jaschke, M. et al, Journal of Physical Chemistry 1996, 100, 2290-2301.*
Bethell, D. et al, Journal of Electroanalytical Chemistry 1996, 409, 137-143.*
Hostetler, M. J. et al, Journal of the American Chemical Society 1996, 118, 4212-4213.*
Andres, R. P. et al, Science 1996, 273, 1690-1693.*
Green, S. J. et al, Journal of Physical Chemistry B 1997, 101, 2663-2668.*
Ingram, R. S. et al, Journal of the American Chemical Society 1997, 119, 9175-9178.*
Wuelfing, W. P. et al, Journal of the American Chemical Society 1998, 120, 12696-12697.*
Lahiri, J. et al, Analytical Chemistry 1999, 71, 777-790.*
Bartz, M. et al, Journal of Materials Chemistry 1999, 9, 1121-1125.*
Evans, S. D. et al, Journal of Materials Chemistry 2000, 10, 183-188.*
Zheng, W. et al, Analytical Chemistry 2000, 72, 2190-2199.*
Labande, A. et al, Chemical Communications 2000, 1007-1008.*
Vanderah, D. J. et al, Langmuir 2000, 16, 6527-6532.*
Han, L. et al, Analytical Chemistry 2001, 73, 4441-4449.*
Shon, Y.-S. et al, Langmuir 2001, 17, 7735-7741.*
Foos, E. E. et al, Chemistry of Materials 2002, 14, 2401-2408.*
Steinecker, W. H. et al, Transducers '03, International Conference on Solid-State Sensors, Actuators and Microsystems, Digest of Technical Papers, 12th, Boston, MA, United States, Jun. 8-12, 2003, vol. 2, 1343-1346, Publisher: Institute of Electrical and Electronics Engineers, New York, N.Y.*
Lover, T. et al, Chemistry of Materials 1997, 9, 1878-1886.*
Szafrankski, C. A. et al, Langmuir 1998, 14, 3580-3589.*
Chen, S. et al, Langmuir 1999, 15, 682-689.*
Chen, S., Langmuir 1999, 15, 7551-7557.*
Templeton, A. C. et al, Accounts of Chemical Research 2000, 33, 27-36.*
Wuelfing, W. P. et al, Journal of Physical Chemistry B 2002, 106, 3139-3145.*
Bain, C. D. et al, Langmuir 1989, 5, 723-727.*
Bain, C. D. et al, Journal of the American Chemical Society 1988, 111, 7155-7164.*
Johnson, S. R. et al, Langmuir 1998, 14, 6639-6647.*

* cited by examiner

CHEMICAL SENSORS BASED ON METAL NANOPARTICLE ENCAPSULATED BY MIXED LIGAND AND SENSOR ARRAY

BACKGROUND

1. Field of the Invention

The present invention relates to a chemical sensor based on metal nanoparticles encapsulated by at least two kinds of mixed ligands and a sensor array using the same.

2. Discussion of Related Art

Depending on the state of the analytes sensing technology can be classified into 'electronic nose' and 'electronic tongue' corresponding respectively to gas phase and liquid phase. Compared with the conventional single chemical sensor whose sensing capability is limited to an analyte composed of a single molecule, a sensor array composed of a number of sensors enables pattern type of sensing for an analyte composed of various kinds of molecules, thus performing mammalian level of sensing. [Julian W. Gardner and Philip N. Bartlett, Electronic Noses: Principles and Applications, Oxford University Press: Oxford, U.K., (1999)].

The sensor array for the pattern type of sensing needs various sensors. Metal oxide sensors have been typically for used that purpose in which their oxidation and reduction characteristics are modified by varying metal catalysts added. [Keith J. Albert, Nathan S. Lewis, Caroline L. Schauer, Gregory A. Sotzing, Shannon E. Stitzel, Thomas P. Vaid, and David R. Walt "Cross-Reactive Chemical Sensor Arrays" Chem. Rev. 100 (2000) 2595-2626]. However, the limit in diversifying the chemical selectivity and the need for power required for high temperature in operation are understood to be the major difficulties in miniaturizing the array systems.

Recently, various sensors or sensor technologies have been developed in the senor array field to overcome those limitations. Among them carbon black-polymer composites and metal nanoparticles encapsulated by molecular monolayer have been gaining interests as sensor materials to overcome the above-mentioned limitations. For example, in the carbon black-polymer complex sensor, conductive carbon black particles are dispersed in a non-conductive polymer matrix to form a sensor film. When the analyte molecules are in contact with the sensor films, the polymer matrix is swollen to increase the distance between the conductive carbon black particles causing increase in the electrical resistance of the sensor composites. [Mark C. Lonergan, Erik J. Severin, Brett J. Doleman, Sara A. Beaber, Robert H. Grubbs, and Nathan S. Lewis "Array-Based Vapor Sensing Using Chemically Sensitive, Carbon Black-Polymer Resistors" Chem. Mater. 8 (1996) 2298-2312]. The easy manipulation of chemical selectivity provided by the diversity of the polymers and the various methods in providing films using for examples spin-coating and dip-coating the composite solutions, are understood to be the major advantages as materials for array technology.

An attempt to use the sensor array in the disease diagnosis is recently drawing attention. The disease diagnosis using this sensor array has been acknowledged as a key merit in that a non-invasive real-time disease diagnosis may be made possible simply using human breath or secretions [Maximilian Fleischer, Elfriede Simon, Eva Rumpel, Heiko Ulmer, Mika Harbeck, Michael Wandel, Christopher Fietzek, Udo Weimar and Hans Meixner, "Detection of volatile compounds corrected to human disease through breath analysis with chemical sensors" Sensors and Actuators B 83 (2002) 245-249]. However, in this sensor array application field, currently, the most difficulty is a limitation of the sensor sensitivity. For example, the gas concentrations related to diseases are on the order of a few ppm to a few ppb. Since the carbon black-polymer complex has a sensitivity limitation in the order of hundreds of ppm over most of the analytes, overcoming the sensitivity limitation is required for use in the disease diagnosis.

With respect to this sensor limitation, a monolayer metal nanoparticle sensor is advantageous. Recently, a gold nanoparticle (2 nm in diameter) sensor encapsulated with octanethiol has been reported to successfully detect a several ppm of toluene [U.S. Pat. No. 6,221,673 to Hank Wohltjen and Arthur W. Snow; Hank Wohltjen and Arthur W. Snow, "Colloidal Metal-Insulator-Metal Ensemble Chimiresistor Sensor" Anal. Chem. 70 (1998) 2856-2859]. This octanethiol-gold nanoparticle, however, has been reported to have a good sensitivity for a non-polar molecule such as toluene or $CCl_4$, while it has a poor sensitivity toward polar molecules. To improve the sensitivity for the polar molecule, the nanoparticles composed of alcohol (—OH) or ethylene oxide ligands has been reported [H-L Zhang, S D Evans, J R Henderson, R E Miles and T-H Shen "Vapour sensing using surface functionalized gold nanoparticles" Nanotechnology 13 (2002) 439-444; Edward E. Foos, Arthur W. Snow, Mark E. Twigg, and Mario G. Ancona "Thiol Terminated Di-, Tri-, and Tetraethylene Oxide Functionalized Gold Nanoparticles: A Water-Soluble, Charge-Neutral Cluster" Chem. Mater. 14 (2002) 2401-2408]. Although the sensitivity was improved (20 ppm for ethanol), problems with regard to response time and signal stability still remain.

SUMMARY OF THE INVENTION

The present invention is directed to a metal nanoparticle sensor with high sensitivity and sensor array that may be applicable to various sensor arrays, that is, a metal nanoparticle sensor that has high stability and reliable sensitivity characteristics, fast reaction characteristics for both polar and non-polar analytes, and various chemical selectivity capable of reacting with various analytes.

Through repeated studies, the inventors have found that for a metal nanoparticle sensor surrounded by the molecule ligand, sensor characteristics such as stability, reaction speed, and chemical selectivity may be adjusted in the metal nanoparticle sensor that is composed of a mixture ligand of preferably but not always at least two kinds of molecule ligands, according to the kind and ratio of the mixture ligand.

In other words, the mixed ligand metal nanoparticle chemical sensor according to the present invention is a metal nanoparticle encapsulated by preferably but not always at least two kinds of different ligands having a relatively low conductivity and various composition ratios.

The mixed ligand metal nanoparticle chemical sensor according to the present invention detects a change of the electrical characteristics due to a change caused by contact or interaction between a detection portion of each ligand and an analyte, wherein the change of the electrical characteristics due to the change caused by the contact or interaction between the ligand detection portion and the analyte is reversible, and particularly, the reversible change of the electrical characteristics may be repeated more than 20 times within an error range of 5%.

Since the sensing properties toward analytes depend on the ligand identity chemical selectivity can be provided by varying the ligand molecules.

Further, the mixed ligand metal nanoparticle chemical sensor according to the present invention may allow pattern type of detection by using a mixed ligand with preferably at least two different detection functional groups (detection portion) as ligand molecules, and may fine tune the selectivity by adjusting the mixture composition of the ligand.

The mixed ligand metal nanoparticle chemical sensor according to the present invention may have a sensitivity below 50 ppm toward the analytes such as alcohol-based (ROH), ester-based, amine-based, carboxyl-based and sulfonic acid-based.

The metal nanoparticle constituting the mixed ligand metal nanoparticle chemical sensor according to the present invention may be gold, silver, platinum or copper particle with a diameter of about 1 nm to 20 nm.

The metal nanoparticle encapsulated by the mixed ligand according to the present invention may be combined through the known nanoparticle composition method. For example, it may be manufactured as described in a document [M. Brust, M. Walker, D. Bethell, D. J. Schiffrin and R. Whyman, J. Chem. Soc., Chem. Commun. (1994) 801-802]; and a document [Michael J. Hostetler, Stephen J. Green, Jennifer J. Stokes, and Royce W. Murray "Monolayers in Three Dimensions: Synthesis and Electrochemistry of omega-Functionalized Alkanethiolate-Stabilized Gold Cluster Compounds" J. Am. Chem. Soc. 1996, 118, 4212-4213].

The ligand is composed of a coupling portion that couples with a surface of the metal nanoparticle and a detection portion that has a detection function, so that a stabilized layer may be formed through an interaction between the detection portions of a plurality of ligands. The coupling portion of the ligand may include thiol (—SH), disulphur (—S—S—), amine (—$NH_2$) functional group, and the detection portion may include a hydrocarbon group having 1 to 18 carbon atoms.

The mixed ligand that controls the selectivity for the analyte may be composed of preferably at least two different molecules. The mixed ligand may be various combinations of chemically or structurally different molecules. These combinations may be made between different series of compounds, or although the molecules are the same series of compound, the combinations may also be between different carbon numbers or functional groups.

The combination of the chemically different molecules may be, for example, between a polar molecule and a non-polar molecule, a combination of a halogen compound and a non-halogen compound, or a cross combination thereof.

The non-polar molecules for example may be composed of an aliphatic hydrocarbon and an aromatic hydrocarbon. The aliphatic hydrocarbon can be composed of a saturated hydrocarbon and an unsaturated hydrocarbon. The halogen compound refers to a hydrocarbon molecule in which hydrogen is substituted by a halogen atom such as F, Cl, Br and I. The polar molecule has the following functional groups, which may have an electric charge:

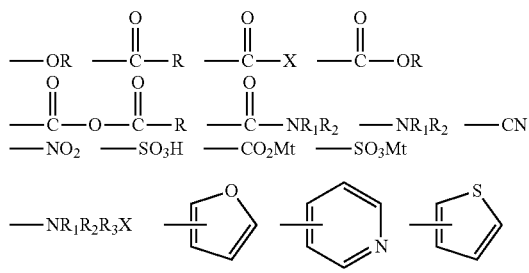

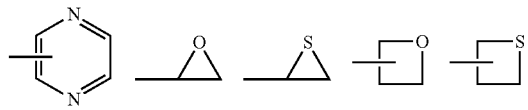

where, R, $R_1$, $R_2$ and $R_3$ may be either the same as or different from each other, and independently represents hydrogen or alkyl group, Mt indicates Li, Na or K metal, and X indicates F, Cl, Br or I.

The combination of structurally different compounds from each other may be made of a combination of a linear molecule and a branched molecule. The linear or branched molecule may be an aliphatic group such as alkane, alkene and alkyne, and the aliphatic group may have an average of 2 to 20 carbon atoms per molecule (a long side for the branched type) while the number of the carbons is not limited when connected in a conjugation. Further, the linear and branched molecules may be combined with the aromatic molecule.

The linear molecules may be substituted by one or more functional group as shown below at the arbitrarily position of an end of the detection portion or between the end and the metal surface:

Y—R—X; Y—R—$NH_2$, Y—R—$NR_1H$, Y—R—N—($R_1R_2$); Y—R—OH, Y—$R_1R_2$O(Ketone), Y—R—CHO, $R_1$—O—$R_2$; Y—RCOOH, $R_1COOR_2$, $RCOOOCR_2$(Anhydride), ROCl or R—CN:

where R, $R_1$, $R_2$ and $R_3$ indicate alkyl, alkenyl, alkynyl, or phenyl group, X indicates F, Cl, Br or I, and Y indicates —SH, —S—S—, —S—SH or —$NH_2$.

The linear molecule constituting a combination of at least two kinds of linear molecules among the mixed ligand may include molecules of the chemical formula illustrated below that has a methylene unit, a functional methylene unit, an aromatic unit, an ethylene oxide unit, an unsaturated

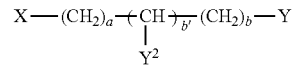

a:b|b' = 2~17

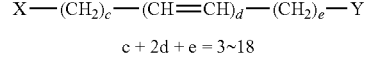

c + 2d + e = 3~18

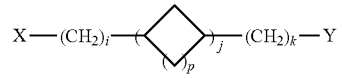

i + 2j + k = 3~18 hydrocarbon unit or an non-aromatic ring unit therein.

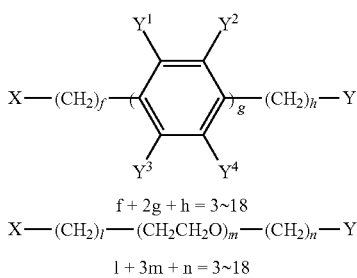

$$f + 2g + h = 3 \sim 18$$

$$X-(CH_2)_l-(CH_2CH_2O)_m-(CH_2)_n-Y$$

$$l + 3m + n = 3 \sim 18$$

where X is —$NH_2$ or —SH, and

Y, $Y^1$, $Y^2$, $Y^3$ and $Y^4$ may be either the same as or different from each other, and —H, —OH, —OR, —NRR', —$CO_2R$, —CONR, —COR, —COOH, —CN, —$NO_2$, —$SO_3$, or —$C_6H_4Z$ (here, substituent Z is —OH, —OR, —NRR', —$CO_2R$, —CONR, —COR, —COOH, —CN, —$NO_2$ or —$SO_3$) and, R is —H, —$CH_3$ or —$CH_2CH_3$.

The aromatic molecule may arbitrarily have 1 to 5 substituents in a benzene ring as shown in the following chemical formula:

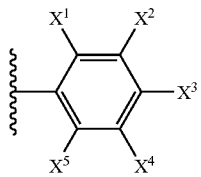

where $X^1$, $X^2$, $X^3$, $X^4$ and $X^5$ are —R, —$NR_1R_2$, —OR, halogen, —$CO_2R$, —$CONR_1R_2$, —$NO_2$ or —CN, and R, $R_1$ and $R_2$ are hydrogen or alkyl group.

Various combinations of the mixed ligand are, though not limited to this, may include a combination of molecules each having a linear portion and an arbitrarily substituted aromatic ring unit in a main chain structure of a molecule; a combination of molecules each having a branched portion and an arbitrarily substituted aromatic ring unit in the main chain structure of the molecule; a combination of a polar molecule and a linear or branched aliphatic non-polar molecule having a detection portion made of only carbon and hydrogen; a combination of a molecule with a polar functional group and a non-polar molecule; and a combination of a linear molecule and a molecule having a branched or aromatic ring.

In particular, the mixed ligand according to the present invention may be a combination of two or more kinds of the following molecules.

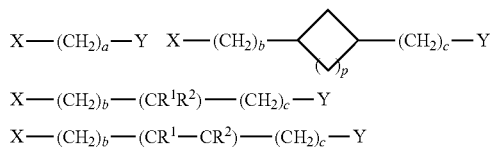

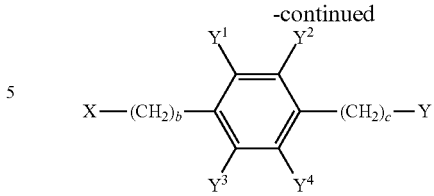

where X is —$NH_2$ or —SH, and

Y is —H, —$CH_3$, —OH, —NRR', —$CO_2R$, —CONR, or —COR, and $Y^1$, $Y^2$, $Y^3$ and $Y^4$ are —H, —$CH_3$, —OH, —NRR', —$CO_2R$, —CONR, or —COR, R and R' are —H or alkyl, and $R^1$ and $R^2$ are —H, —$CH_3$, —$CH_2CH_3$, —$CH_2CH_2CH_3$, —OH, —NRR', —$CO_2R$, —CONR, or —COR, and a is 3 to 18, and b and c are 0 to 16, and b+c is 0 to 16, and p is 2, 3 or 4.

These combinations may be made by configuring the same series of molecules to have either different carbon numbers or functional groups from each other, or by a combination of different series from each other.

The sensor array in which the mixed ligand metal nanoparticle chemical sensor according to the present invention is arranged may be manufactured by forming on a substrate as a film, a polymer solution in which the metal nanoparticle attached with a mixed ligand is dispersed, using a spin coating method, a dip coating method, and other known various methods.

BRIEF DESCRIPTION OF THE DRAWINGS

The above and other features and advantages of the present invention will become more apparent to those of ordinary skill in the art by describing in detail the preferred embodiments thereof with reference to the attached drawings in which.

DETAILED DESCRIPTION OF PREFERRED EMBODIMENTS

Figure 1:
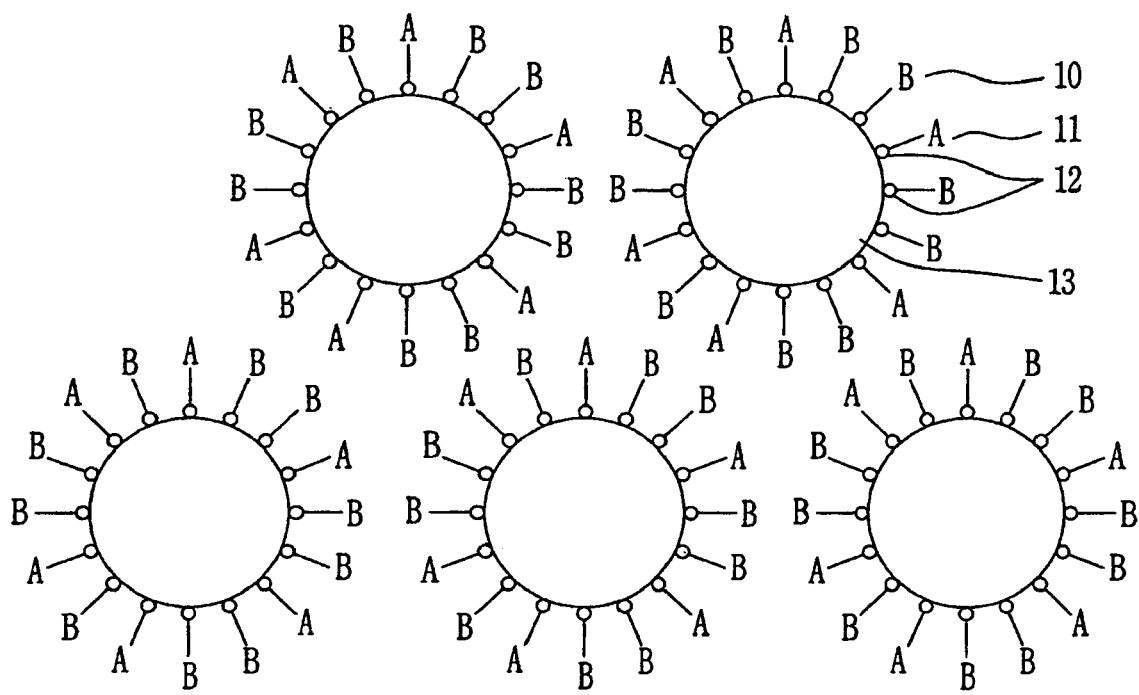
FIG. 1 is a schematic diagram showing a structure of a mixed ligand metal nanoparticle composed of two kinds of ligand molecules.

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will fully convey the scope of the invention to those skilled in the art.

EMBODIMENT

A mixed ligand metal nanoparticle chemical sensor according to the present invention may be manufactured by a conventional known synthesis method. That is, it may be manufactured by a method disclosed in the document [M. Brust, M. Walker, D. Bethell, D. J. Schiffrin, R. Whyman, J. Chem. Soc., Chem. Commun. (1994) 801-802.] and a document [Michael J. Hostetler, Stephen J. Green, Jennifer J. Stokes, and Royce W. Murray "Monolayers in Three Dimensions: Synthesis and Electrochemistry of omega-Functionalized Alkanethiolate-Stabilized Gold Cluster Compounds" J. Am. Chem. Soc. 1996, 118, 4212-4213.]

Comparative Example 1

Manufacturing a single toluene ligand gold nanoparticle sensor (S5)

An $HAuCl_4$ (1.7 g) solution dissolved in distilled water (150 ml) and a tetraoctylammonium bromide (10 g) solution dissolved in toluene (400 ml) were mixed in a reaction container. After dissolving equimolar amount of para-toluenethiol (1.1 g) and $HAuCl_4$ in toluene (5 ml), aqueous solution of sodium borohydride (1.9 g) was added and stirred for 3 hours. The products were precipitated and filtered in ethanol and the solvent was evaporated under reduced pressure to obtain the nanoparticle products (S5) having a single toluene ligand (96% yield).

Embodiment 1

Manufacturing a mixed ligand gold nanoparticle (S1) with a ratio of toluene: 4-mercaptophenol=1:0.22

The single toluene ligand metal nanoparticle manufactured in the first embodiment and 4-mercaptophenol of 13.9 mg were mixed and stirred in a THF solvent of 100 mg to synthesize a toluene-4-mercaptophenol mixed ligand gold nanoparticle product. After completing the reaction, the product was dispersed and filtered in diethyleter and the solvent was evaporated under the reduced pressure to obtain the final toluene-4-mercaptophenol mixed ligand gold nanoparticle (S1).

Embodiments 2 to 4

Sensors having various ligand compositions as shown in Table 1 were manufactured by changing an amount of mercaptophenol in the same manner as embodiment 1.

TABLE 1

| Embodiment | Sensor | Molar ratio between ligand —PhCH3 and —PhOH |
|---|---|---|
| Embodiment 1 | S1 | 1.0:0.22 |
| Embodiment 2 | S2 | 1.0:0.64 |
| Embodiment 3 | S3 | 1.0:1.92 |
| Embodiment 4 | S4 | 1.0:10.0 |
| Comparative Example 1 | S5 | 1.0:0.0 |

Embodiment 5

Each sensor particle of 25 mg listed in Table 1 was put into chloroform of 1 ml, and was sonicated for two minutes to make a gold nanoparticle sensor dispersion solution. A glass substrate mounted with interdigitated gold electrode was immersed in $H_2SO_4/H_2O_2$ (3:1 v/v) for 1 minute and dried by acetone and distilled water, and then was dipped in the nanoparticle dispersion solution to form a sensor layer and was dried in the air for 24 hours.

Embodiment 6

CBMT-OT Mixed Ligand Synthesis Embodiment (SB)

Tetraoctylammonium bromide (5.5 g, 10.0 mmol) was dissolved in toluene of 240 ml, and then, was added to the distilled water of 120 ml in which $HAuCl_4$ (1.6 g, 4.0 mmol) was dissolved. After stirring for 2 minutes, 4-chlorobenzenemethanethiol (0.32 g, 2.0 mmol) was added, and sodiumborohydride of 0.8 g was dissolved in water to be added to the reaction mixture of 50 ml. Then it was precipitated in methanol, filtered, and dried to obtain 4-chlorobenzenemethanethiol (CBMT) nanoparticle.

CBMT nanoparticle of 0.15 g was dispersed in chloroform of 15 ml, and n-octanethiol (11.7 mg) was added, stirred and dispersed in acetonitrile, and then, is filtered to obtain the mixed ligand nanoparticle. The nanoparticle was manufactured in a film by the dip-coating method in the same manner as the nanoparticle sensor described above.

Example

Figure 4:
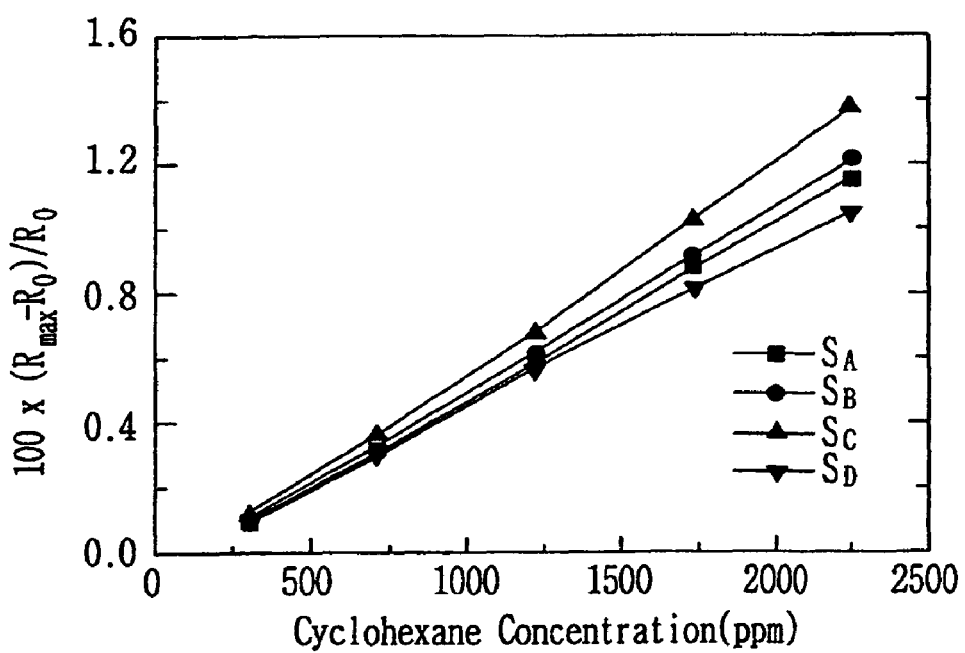
FIG. 4 is a graph of a detection characteristic obtained by changing a concentration of cyclohexane from about 300 ppm to 2300 ppm, of four sensors composed of a mixed ligand of CBMT and OT.

FIG. 4 describes detection behavior, obtained by changing a concentration of cyclohexane from about 300 ppm to 2300 ppm, of four sensors shown in Table 2 composed of a mixed ligand of CBMT and OT, in the same manner as described above. As shown in FIG. 4, differential maximum relative resistance $100 \times (R_{max} - R_0)/R_0$ was listed according to the composition change, which showed linearity in the given concentration range.

Sensors having various ligand compositions as shown in Table 2 were manufactured by changing an amount of mercaptophenol in the same manner as Embodiment 6.

TABLE 2

| Sensor type | Molar ratio (OT:CBMT) |
|---|---|
| SA | 0.0:1.0 |
| SB | 0.42:1.0 |
| SC | 0.79:1.0 |
| SD | 1.36:1.0 |

Example

For a series of mixed ligand gold thin film sensors prepared above, the detection characteristics were surveyed using a gas detection measurement device in which a flow control system is arranged.

Example 1

Five different sensors manufactured from the embodiment 5 were put into the gas detection measurement device, and ethanol evaporation concentration was kept to remain 670 ppm, and then a resistance change of each sensor was measured according to an elapsed time. After 100 seconds following ethanol gas injection, the injection of the ethanol gas was stopped to infuse and the resistance change was also measured. These resistance measurement values were converted into relative resistance change ($100\times(R-R_0)/R_0$), where R refers to a resistance value of a sensor when ethanol gas was infused, and $R_0$ refers to a baseline resistance value when air was provided, and the result was shown in FIG. 2.

Figure 2:
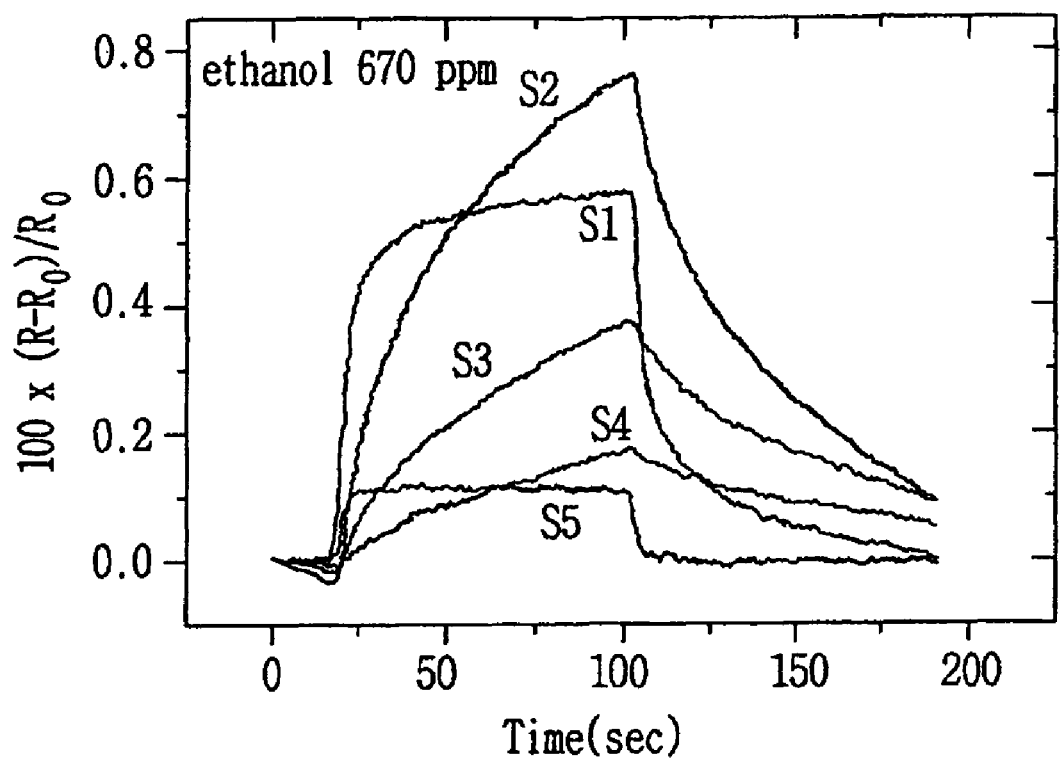
FIG. 2 is a graph showing a detection characteristic for an ethanol gas of a mixed ligand gold nanoparticle sensor synthesized in accordance with an exemplary embodiment of the present invention.

The FIG. 2 showed that as the ethanol gas sample was infused, the resistance values of the five sensors were generally increased while as the air was injected instead of the ethanol, the resistance values were reduced. However, compared with the detection characteristics (resistance change) of the sensor S5 formed only with toluene ligand, the mixed ligand sensors S1, S2, S3 and S4 had a higher amplitude (sensitivity) in resistance change, and a shorter time to reach a certain level of resistance value (reaction time). In particular, with respect to the resistance change, S1 reacted with the ethanol, which is a polar molecule, 5 times larger than the nanoparticle sensor S5 composed of only the toluene ligand. Also S1 was characterized with faster reaction time than other mixed ligand sensors.

Since the metal nanoparticles with the mixed ligand S1, S2, S3, and S4 had different ranges (sensitivity) of resistance change and different times to reach a certain level of resistance value (reaction speed), the sensitivity and the reaction speed of the sensor could be controlled by adjusting a composition ratio of the mixed ligand.

When taking advantage of the dependence of the reaction time and response change on the variation of the mixture composition, chemical selectivity which may be expressed by signal amplitude and reaction time (selectivity may also be indicated by the slope of the signal trace or the time to reach a certain portion of the equilibrium response) may be diversified. Also the experiments underwent in this invention show that the limit experienced in the monoligand nanoparticles, in which the chemical selectivity is provided by variation of ligand molecules, can be overcome to provide wider ranges of chemical selectivity. It is expected that this mixed ligand nanoparticle sensor capable of improving the sensor performance and implementing various selectivity may significantly improve the existing sensor array technology.

Example 2

Five kinds of sensor arrays manufactured from the embodiment 5 were put into the gas detection measurement device, and then ethanol, acetone, chloroform, n-hexane and i-propanol gases were added in a concentration of 1800 ppm, and a resistance value change of each sensor array was measured. The maximum value of these resistance measurement values was converted into a relative resistance change ratio ($100\times(R-R0)/R0$), where R refers to a resistance value of a sensor when ethanol gas was given, and R0 refers to a baseline resistance value, and the result was shown in FIG. 3 as a bar graph.

Figure 3:
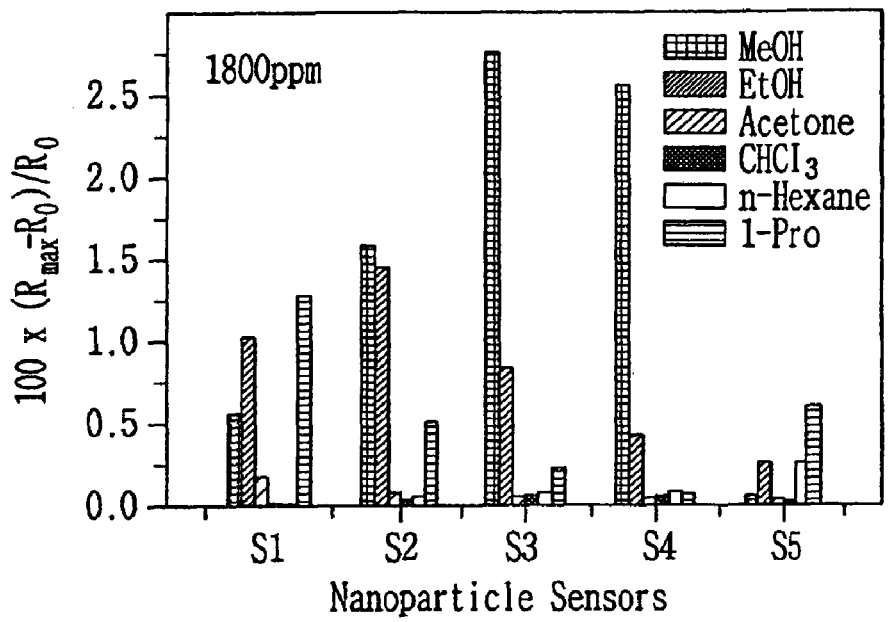
FIG. 3 is a graph showing chemical selectivity of a mixed ligand gold nanoparticle sensor synthesized in accordance with an exemplary embodiment of the present invention, for various chemical solvent gases.

From FIG. 3, it could be appreciated that detection selectivity for various analyte gases may be diversified with the metal nanoparticle sensor using the mixed ligand according to the present invention.

For the mixed ligand metal nanoparticle sensor according to the present invention, the detection characteristics of the sensor are regularly varied according to a composition ratio of the mixed ligand as shown in FIG. 2, and its detection characteristics are varied according to the analyte even with the same mixed ligand as shown in FIG. 3, thus having a significant meaning in the sensor array technology since design and fabrication of the sensor characteristic required with respect to several analytes may be enabled. That is, a configuration of the sensor array suitable for the analysis using the sensor array is a key factor in accuracy of the analysis, in which the design and fabrication of the sensor having the required detection characteristics may lead to very efficient fabrication of the sensor array through a systematic configuration of the sensor array.

As described above, with the metal nanoparticle sensor using the mixed ligand according to the present invention, the sensitivity and the reaction speed with respect to the analyte are improved, selectivity with respect to various analytes is good, and a type and a composition of the mixed ligand constituting the metal nanoparticle sensor are adjusted to apply the high sensitivity nanoparticle sensor to the sensor array technology. Further, the type and the composition ratio of the mixed ligand are adjusted to allow a design of the sensor characteristics, thus enabling a systematic approach of the most efficient sensor array configuration with respect to the subject to be analyzed. The application of this high sensitivity nanoparticle sensor to the array technology is expected to attribute to the non-invasive real-time disease diagnosis technology through human breathing gas and other secretions.

Although the present invention has been described in detail by way of the detailed embodiments, the present invention is not limited to the embodiments, and it will be apparent that variations and modifications may be made to the present invention by those skilled in the art without departing from the technical spirit of the present invention.

What is claimed is:

1. A metal nanoparticle chemical gas sensor, comprising:
a substrate having an interdigitated electrode; and
a metal nanoparticle comprising gold, silver, platinum, or copper;
wherein the metal nanoparticle is on the substrate;
wherein the metal nanoparticle has at least two different ligands encapsulated on a surface;
wherein the at least two different ligands are chosen from those of formula (I)

wherein Y is chosen from S, S—S, and NH;
wherein R is phenyl;
wherein X is OH for one of the at least two different ligands; and
wherein X is $CH_3$ for one of the at least two different ligands.

2. A metal nanoparticle chemical gas sensor of claim 1, wherein the at least two different ligands encapsulated on a surface are formed from para-toluenethiol and 4-mercaptophenol, and wherein the para-toluenethiol ligand to 4-mercaptophenol ligand mole ratio between the at least two different ligands ranges from 1.0:0.22 to 1.0:10.0.

* * * * *